(12) United States Patent
Kawabata et al.

(10) Patent No.: US 10,939,037 B2
(45) Date of Patent: Mar. 2, 2021

(54) CAPSULE ENDOSCOPE, RECEIVING DEVICE, OPERATION METHOD OF CAPSULE ENDOSCOPE, AND COMPUTER READABLE RECORDING MEDIUM

(71) Applicant: OLYMPUS CORPORATION, Tokyo (JP)

(72) Inventors: Yuya Kawabata, Hachioji (JP); Kazuhiko Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 32 days.

(21) Appl. No.: 16/353,291

(22) Filed: Mar. 14, 2019

(65) Prior Publication Data

US 2019/0208123 A1 Jul. 4, 2019

Related U.S. Application Data

(63) Continuation of application No. PCT/JP2017/038388, filed on Oct. 24, 2017.

(30) Foreign Application Priority Data

Nov. 7, 2016 (JP) .............................. JP2016-217477

(51) Int. Cl.
*H04N 5/232* (2006.01)
*A61B 1/04* (2006.01)
(Continued)

(52) U.S. Cl.
CPC ........... *H04N 5/23232* (2013.01); *A61B 1/00* (2013.01); *A61B 1/00009* (2013.01);
(Continued)

(58) Field of Classification Search
None
See application file for complete search history.

(56) References Cited

U.S. PATENT DOCUMENTS 6,709,387 B1    3/2004  Glukhovsky et al.
8,611,621 B2 *  12/2013 Drozdzal ............... A61B 1/041
                                                   382/128
(Continued)

FOREIGN PATENT DOCUMENTS

JP    2004-521662 A    7/2004
JP    2005-193066 A    7/2005
(Continued)

OTHER PUBLICATIONS

International Search Report dated Jan. 16, 2018 issued in PCT/JP2017/038388.

*Primary Examiner* — Bernard Krasnic
(74) *Attorney, Agent, or Firm* — Scully, Scott, Murphy & Presser, P.C.

(57) ABSTRACT

A capsule endoscope includes: an image sensor configured to generate an image by capturing inside a subject at an imaging frame rate that is variable; and a processor comprising hardware, the processor being configured to determine whether the image is a first image whose feature amount related to a region having a bubble or a residue imaged is equal to or greater than a predetermined amount, and change the imaging frame rate based on a determination result.

12 Claims, 17 Drawing Sheets

(51) Int. Cl.
*A61B 1/045* (2006.01)
*A61B 1/00* (2006.01)
*H04N 5/225* (2006.01)

(52) U.S. Cl.
CPC .............. *A61B 1/041* (2013.01); *A61B 1/045* (2013.01); *H04N 2005/2255* (2013.01)

(56) References Cited

U.S. PATENT DOCUMENTS

| | | |
|---|---|---|
| 2005/0250991 A1 | 11/2005 | Mizuno |
| 2008/0068454 A1* | 3/2008 | Hirakawa ............. G06T 7/0012 |
| | | 348/65 |
| 2008/0242931 A1 | 10/2008 | Nishino |
| 2012/0155724 A1* | 6/2012 | Kitamura ................ G06T 7/12 |
| | | 382/128 |

FOREIGN PATENT DOCUMENTS

| | | |
|---|---|---|
| JP | 2007-236700 A | 9/2007 |
| JP | 2007-313119 A | 12/2007 |
| JP | 2008-237639 A | 10/2008 |
| JP | 2009-056205 A | 3/2009 |
| JP | 2012-071186 A | 4/2012 |
| JP | 2012-143340 A | 8/2012 |
| WO | WO 2012/165299 A1 | 12/2012 |

* cited by examiner

FIG.8

|  | DETERMINE TO BE BUBBLE RESIDUE IMAGE | DETERMINE NOT TO BE NOT BUBBLE RESIDUE IMAGE |
|---|---|---|
| MOVEMENT IS LARGE | MAINTAIN FRAME RATE | MAINTAIN FRAME RATE |
| MOVEMENT IS SMALL | DECREASE FRAME RATE | MAINTAIN FRAME RATE |

CAPSULE ENDOSCOPE, RECEIVING DEVICE, OPERATION METHOD OF CAPSULE ENDOSCOPE, AND COMPUTER READABLE RECORDING MEDIUM

CROSS-REFERENCE TO RELATED APPLICATION

This application is a continuation of PCT International Application No. PCT/JP2017/038388 filed on Oct. 24, 2017 which claims the benefit of priority from Japanese Patent Application No. 2016-217477, filed on Nov. 7, 2016, the entire contents of which are incorporated herein by reference.

BACKGROUND

The present invention relates a capsule endoscope, a receiving device, an operation method of the capsule endoscope, and a computer readable recording medium.

In the field of endoscopy, a capsule endoscope that is introduced into a subject and captures images has been developed. The capsule endoscope has an imaging function and wireless communication function inside a capsule shaped casing that is formed such that it can be introduced into the digestive tract of the subject. After the capsule endoscope has been swallowed by the subject, the capsule endoscope performs imaging while moving inside the digestive tract by a peristaltic movement, sequentially generates images (hereinafter, also referred to as in-vivo images) inside the organ of the subject, and wirelessly transmits the images (for example, see International Publication Pamphlet No. WO 2012/165299). The wirelessly transmitted images are received by a receiving device provided outside the subject; are further acquired by an image processing device, such as a workstation or the like; and are subjected to predetermined image processing. Consequently, it is possible to display in-vivo images of the subject as still images or moving images on a display unit of the image processing device.

SUMMARY

A capsule endoscope according to one aspect of the present disclosure includes: an image sensor configured to generate an image by capturing inside a subject at an imaging frame rate that is variable; and a processor comprising hardware, the processor being configured to determine whether the image is a first image whose feature amount related to a region having a bubble or a residue imaged is equal to or greater than a predetermined amount, and change the imaging frame rate based on a determination result.

A receiving device according to another aspect of the present disclosure includes: a receiver configured to receive an image from a capsule endoscope including an image sensor that generates the image by capturing inside a subject at an imaging frame rate that is variable; a processor comprising hardware, the processor being configured to determine whether the image is a first image whose feature amount related to a region having a bubble or a residue imaged is equal to or greater than a predetermined amount, and generate, based on a determination result, control information related to control of the imaging frame rate; and a transmitter configured to transmit the control information to the capsule endoscope.

The above and other features, advantages and technical and industrial significance of this invention will be better understood by reading the following detailed description of presently preferred embodiments of the disclosure, when considered in connection with the accompanying drawings.

BRIEF DESCRIPTION OF THE DRAWINGS

FIG. 8 is a diagram illustrating a condition for setting, by a frame rate setting unit, an imaging frame rate based on determination results obtained by an image determination unit and a movement determination unit;

DETAILED DESCRIPTION

Figure 1:
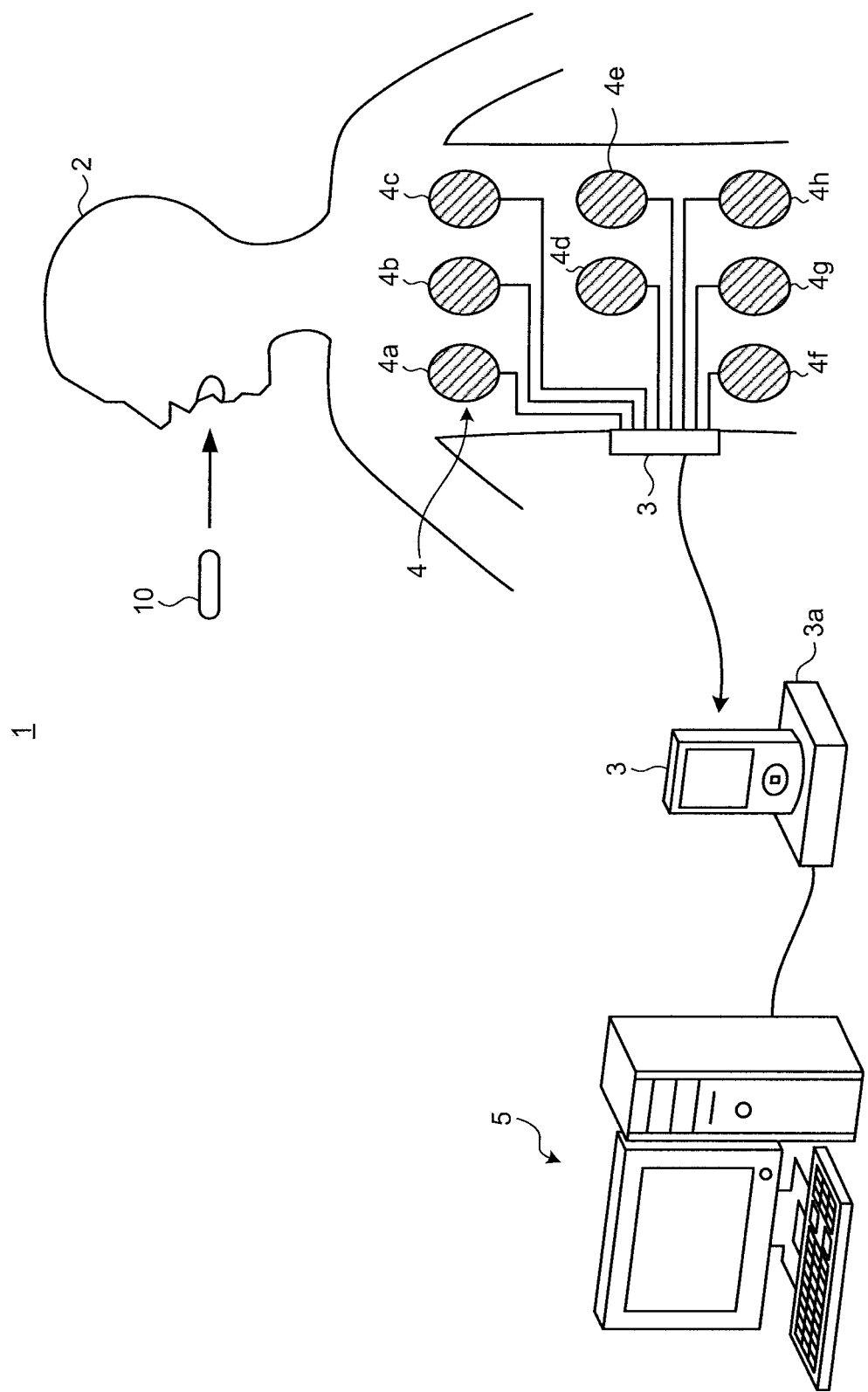
FIG. 1 is a schematic diagram illustrating, in outline, the configuration of a checking system including a capsule endoscope according to a first embodiment.

Preferred embodiments of a capsule endoscope, a receiving device, an operation method of the capsule endoscope, and an operation program of the capsule endoscope according to the present disclosure will be described with reference to accompanying drawings. Furthermore, the present disclosure is not limited to the embodiments. The present disclosure can be typically applied to a capsule endoscope, a receiving device, an operation method of the capsule endoscope, and an operation program of the capsule endoscope.

In the following, in the drawings, components that are identical to those in embodiments are assigned the same reference numerals. The drawings used for the descriptions below are only schematic illustrations. The relationship between the thickness and the width of each member, the proportions of each member, and so on are different from those used in practice. The size or reduction in scale of elements may sometimes differ between the drawings.

First Embodiment

FIG. 1 is a schematic diagram illustrating, in outline, the configuration of a checking system including a capsule endoscope according to a first embodiment. A checking system 1 illustrated in FIG. 1 includes a capsule endoscope 10 that is introduced into a subject 2, such as a patient, that performs imaging, that generates images, and that wirelessly transmits the images; a receiving device 3 that receives the images, which have been wirelessly transmitted from the capsule endoscope 10, via a receiving antenna unit 4 that is mounted on the subject 2; and an image processing device 5 that acquires the images from the receiving device 3, that performs predetermined image processing on the images, and that displays the images.

Figure 2:
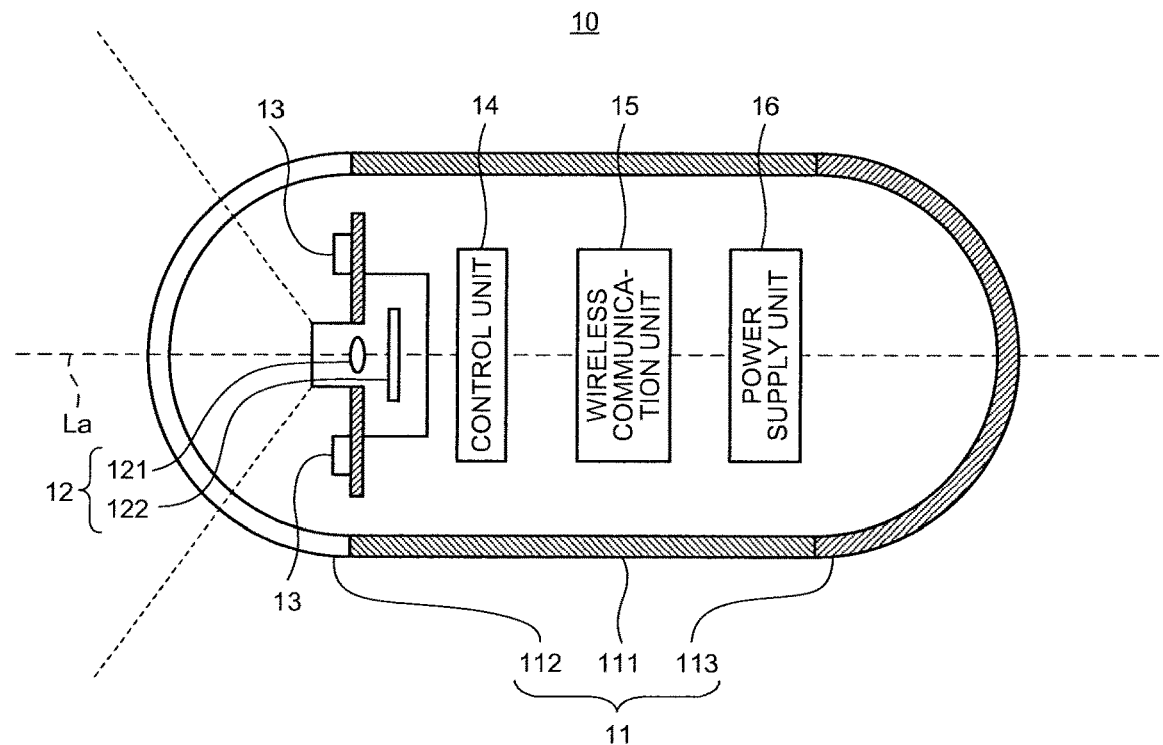
FIG. 2 is a schematic diagram illustrating a configuration example of the capsule endoscope according to the first embodiment.

FIG. 2 is a schematic diagram illustrating a configuration example of the capsule endoscope according to the first embodiment. After having been orally introduced inside the subject 2, the capsule endoscope 10 is moved in the interior of the digestive tract and is finally discharged outside the subject 2. During this period of time, while moving inside the organ (the digestive tract) by a peristaltic movement, the capsule endoscope 10 performs imaging inside the subject 2, sequentially generates images, and wirelessly transmits the images.

As illustrated in FIG. 2, the capsule endoscope 10 includes a capsule-shaped casing 11 that is an outer casing formed in a size that can be easily introduced into an interior of the organ of the subject 2; an imaging unit 12 that performs imaging inside the subject 2 at a variable imaging frame rate and that generates an image signal; an illumination unit 13 that generates light for illuminating inside the subject 2; a control unit 14 that generates images by performing image processing on the image signal that has been input from the imaging unit 12 and that controls each of the component units in the capsule endoscope 10; a wireless communication unit 15 that wirelessly transmits the images generated by the control unit 14 to outside the capsule endoscope 10; and a power supply unit 16 that supplies electrical power to each of the component units in the capsule endoscope 10.

The capsule-shaped casing 11 is formed by a cylindrical casing 111 and dome shaped casings 112 and 113 and is implemented by covering both ends of the openings of the cylindrical casing 111 by the dome shaped casings 112 and 113. The cylindrical casing 111 and the dome shaped casing 113 are substantially opaque and colored casing with respect to visible light. In contrast, the dome shaped casing 112 is an optical member that is transparent with respect to light having a predetermined wavelength band, such as visible light, and that has a dome shape. The capsule endoscope 10 described above contains, in a liquid-tight manner, the imaging unit 12, the illumination unit 13, the control unit 14, the wireless communication unit 15, and the power supply unit 16.

The imaging unit 12 includes an optical system 121, such as a condenser lens, and an image sensor 122 formed by a complementary metal oxide semiconductor (CMOS) image sensor or a charge coupled device (CCD) image sensor. The optical system 121 condenses the light reflected from the imaging field of view and forms an image on an imaging surface of the image sensor 122. The image sensor 122 converts the light (light signal), which has been received on the imaging surface and reflected from the imaging field of view, to an electrical signal and then outputs the image signal.

The illumination unit 13 is formed of a light-emitting element, such as a light emitting diode (LED) or a laser diode (LD), and emits illumination light, such as white light. The illumination unit 13 illuminates the subject 2 in the imaging field of view of the image sensor 122 with illumination light through the dome shaped casing 112.

Furthermore, in the first embodiment, the capsule endoscope 10 with a monocular type that captures one of the end portions of the capsule endoscope 10 in the direction of a major axis La is used; however, a pantoscopic capsule endoscope that captures both ends (front and rear) of the capsule endoscope 10 in the direction of the major axis La may also be used. In this case, it is preferable to arrange each of the optical axes of the two imaging units so as to be substantially parallel with or substantially matched with the major axis La of the capsule-shaped casing 11 and to arrange each imaging field of view faces the opposite direction each other. Namely, the imaging surface of the image sensor included in each of the imaging units is placed so as to be orthogonal to the major axis La.

Figure 3:
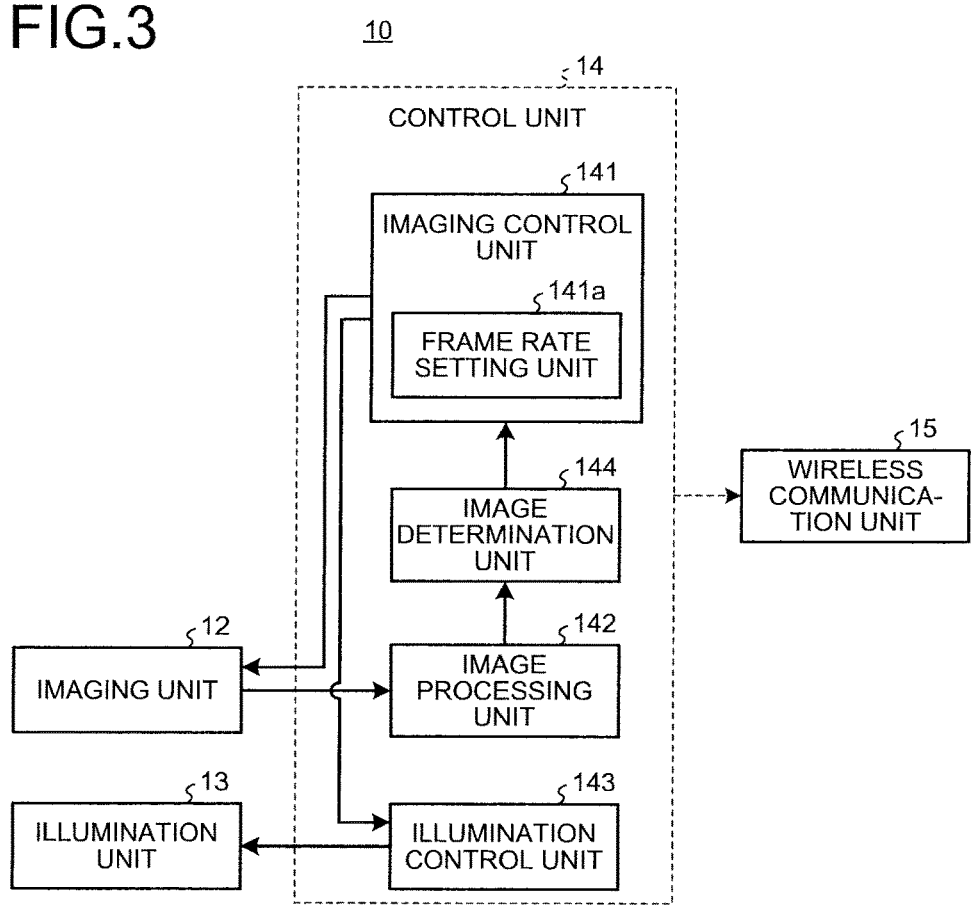
FIG. 3 is a block diagram illustrating a configuration of the capsule endoscope according to the first embodiment.

The control unit 14 controls operation of each of the component units in the capsule endoscope 10 and controls an input/output of a signal between these component units. The control unit 14 is formed by using a general purpose processor, such as a central processing unit (CPU), or a special purpose processor, such as various arithmetic circuits or the like including an application specific integrated circuit (ASIC) or a field programmable gate array (FPGA). FIG. 3 is a block diagram illustrating a configuration of the capsule endoscope according to the first embodiment. As illustrated in FIG. 3, the control unit 14 includes an imaging control unit 141, an image processing unit 142, an illumination control unit 143, an image determination unit 144, and a frame rate setting unit 141a. Furthermore, in FIG. 3, illustrations of the capsule-shaped casing 11, the power supply unit 16, and the like that have been described with reference to FIG. 2 are omitted.

The imaging control unit 141 controls an imaging operation, such as an imaging frame rate, at the time at which the imaging unit 12 performs imaging and outputs, to the illumination control unit 143, instruction information that is used to control an amount of light emitted from the illumination unit 13. Specifically, the imaging control unit 141 changes the imaging frame rate at the imaging unit 12 based on the determination result determined by the image determination unit 144. Furthermore, the imaging control unit 141 includes the frame rate setting unit 141a that sets an imaging frame rate. Specifically, if an image that has been determined not to be useful for observation by the image determination unit 144 continues by an amount equal to or greater than a predetermined amount, the frame rate setting unit 141a sets the imaging frame rate to be decreased. The predetermined amount is, for example, the number of images; however, the predetermined amount may also be a continuous period of time for which the image that has been determined not to be useful for observation continues or a continued distance (the distance between the points of the capsule endoscope 10 moved when the image was being captured). Furthermore, the continued distance can be calculated by using the radio field intensity for each image received by the receiving antenna unit 4. Furthermore, in the first embodiment, a description will be given with the assumption that a predetermined number of images is three; however, the number of images is not particularly limited. Then, the imaging control unit 141 changes the imaging frame rate in the imaging unit 12 based on the imaging frame rate set by the frame rate setting unit 141a.

The image processing unit 142 performs predetermined image processing on the image signal output from the imaging unit 12 (the image sensor 122) and generates an image.

The illumination control unit 143 controls an amount of light emitted from the illumination unit 13 or emission time based on the instruction information obtained from the imaging control unit 141.

The image determination unit 144 determines whether the image that has been subjected to image processing by the image processing unit 142 is useful for observation. The image that is not useful for observation is a bubble residue image that is an image in which, for example, a feature amount related to a region having a bubble or a residue imaged is equal to or greater than a predetermined amount. The feature amount is, for example, an area of the region in which a bubble or a residue is imaged; however, the feature amount may also be an amount calculated by using the number of pixels in the region in which a bubble or a residue is imaged, an area ratio, a ratio of the number of pixels, a position in which a bubble or a residue is imaged, or the like.

Furthermore, a region in which a bubble or a residue is imaged can be detected by using a known method. For example, as disclosed in Japanese Laid-open Patent Publication No. 2007-313119, a bubble region may also be detected by performing matching between a bubble model, which is set based on the characteristic of a bubble image, such as an arc shaped convex edge generated due to illumination reflection that is present in a contour portion of the bubble and inside the bubble, and an edge, which has been extracted from an intraluminal image. Furthermore, as disclosed in Japanese Laid-open Patent Publication No. 2012-143340, it may also be possible to detect a residue candidate region that is assumed to be a non-mucosal region based on color features obtained based on each of pixel values and then determine whether a residue candidate region is a mucosa region based on the positional relationship between this residue candidate region and the edge that has been extracted from the intraluminal image.

The wireless communication unit 15 acquires an image from the control unit 14, generates a radio signal by performing a modulation process on the image, and transmits the signal to the receiving device 3.

The power supply unit 16 is a storage battery unit, such as a button type battery or a capacitor, and includes a switch unit, such as a magnetic switch or an optical switch. When the power supply unit 16 is constituted by including a magnetic switch, the power supply unit 16 switches an on/off state of a power supply by using the magnetic field applied from outside. In a case of an on state, the power supply unit 16 supplies electrical power of the storage battery unit to each of the component units (the imaging unit 12, the illumination unit 13, the control unit 14, and the wireless communication unit 15) in the capsule endoscope 10, whereas, in a case of an off state, the power supply unit 16 stops the supply of electrical power to each of the component units in the capsule endoscope 10.

Furthermore, in FIG. 2, the configuration in which the capsule endoscope 10 is passively moved due to a peristaltic movement of the subject 2 has been described as a configuration example; however, it may also be possible to use a configuration in which the capsule endoscope 10 can move inside the subject 2 by using the own driving force or based on being guided from outside. For example, the capsule endoscope may also be guided inside the subject 2 by providing a permanent magnet inside the capsule endoscope and allowing the permanent magnet to act the magnetic field generated outside the subject 2.

A description will be given here by referring back to FIG. 1. The receiving antenna unit 4 includes a plurality of receiving antennas 4a to 4h (8 pieces in FIG. 1). Each of the receiving antennas 4a to 4h is implemented by using, for example, a loop antenna and is arranged at a predetermined position (for example, the position that is associated with each of the organ in the subject 2 and that is a region in which the capsule endoscope 10 passes) on an outer surface the body of the subject 2.

The receiving device 3 receives, via the receiving antennas 4a to 4h, the images that have been wirelessly transmitted from the capsule endoscope 10, performs a predetermined process on the received images, and stores the images and the information related to the images in a built-in memory. It may also be possible to provide, in the receiving device 3, a display unit that displays a receiving state of an image that has been wirelessly transmitted from the capsule endoscope 10 of an input unit, such as an operation button, for operating the receiving device 3. Furthermore, the receiving device 3 is constituted by including a general purpose processor, such as a CPU, or a special purpose processor, such as various arithmetic circuits, that executes a special function of an ASIC, an FPGA, or the like.

The image processing device 5 is configured by using a work station or a personal computer including, for example, a general purpose processor, such as a CPU, or a special purpose processor, such as various arithmetic circuits, that executes a special function of an ASIC, an FPGA, or the like. The image processing device 5 fetches the images stored in the memory in the receiving device 3 and the information related to the images and performs predetermined image processing, thereby the image processing device 5 generates in-vivo images inside the subject 2 and displays the generated images on the screen. Furthermore, in FIG. 1, the structure is configured such that, by connecting a cradle 3a to a USB port in the image processing device 5 and by setting the receiving device 3 on the cradle 3a, the receiving device 3 is connected to the image processing device 5 and the images and the information related to the images are transferred from the receiving device 3 to the image processing device 5.

Figure 4:
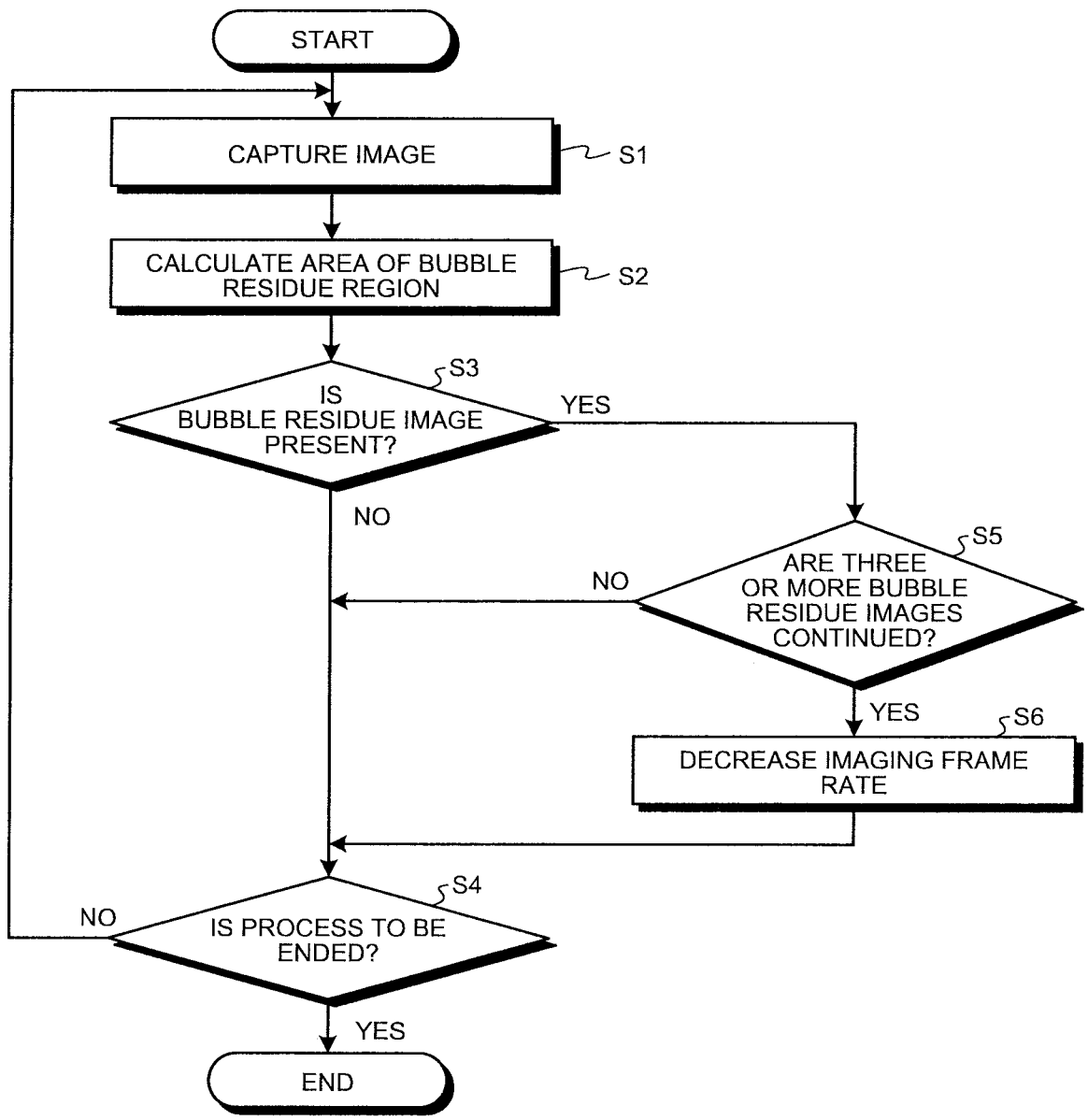
FIG. 4 is a flowchart illustrating the flow of an operation of the capsule endoscope according to the first embodiment.

In the following, an operation of the capsule endoscope 10 will be described. FIG. 4 is a flowchart illustrating the flow of an operation of the capsule endoscope according to the first embodiment. When the power supply of the capsule endoscope 10 is turned on and an operation is started, first, the imaging unit 12 captures, under the control of the imaging control unit 141, an image inside the subject 2 (Step S1).

Then, the image determination unit 144 calculates the area of the region in which a bubble or a residue is imaged in the image captured in the imaging unit 12 (Step S2). Furthermore, the image determination unit 144 determines whether the region in which the bubble or the residue is imaged in the image is a bubble residue image having an area equal to or greater than a predetermined area (Step S3).

If the image determination unit 144 determines that the region is not the bubble residue image (No at Step S3), the imaging control unit 141 determines whether an instruction to end the capturing has been input (Step S4). If an instruction to end the capturing has been input (Yes at Step S4), a series of processes is ended. In contrast, if an instruction to end the capturing has not been input (No at Step S4), the process returns to Step S1 and the process is repeatedly performed on the image in the subsequent frame captured by the imaging unit 12.

At this time, if the image determination unit 144 determines that the region is a bubble residue image (Yes at Step S3), the frame rate setting unit 141a determines whether three or more bubble residue images continue (Step S5).

If the frame rate setting unit 141a determines that three or more bubble residue images continue (Yes at Step S5), the frame rate setting unit 141a sets an imaging frame rate in the imaging unit 12 to be decreased. Then, the imaging control unit 141 decreases the imaging frame rate in the imaging unit 12 based on the setting determined by the frame rate setting unit 141a (Step S6). Thereafter, it is determined whether the process at Step S4 is to be ended and then the process is continued or ended.

In contrast, if the frame rate setting unit 141a determines that three or more bubble residue images do not continue (No at Step S5), it is determined whether the process at Step S4 is to be ended and then the process is continued or ended.

As described above, according to the first embodiment, if the capsule endoscope 10 is located at the position in which an image that is useful for observation is not able to be captured due to a lot of bubbles or residues, the imaging frame rate in the imaging unit 12 is automatically decreased. Consequently, the capsule endoscope 10 can suppress consumption of a battery and suppress capturing of an image that is not useful for observation.

Modification 1-1

Figure 5:
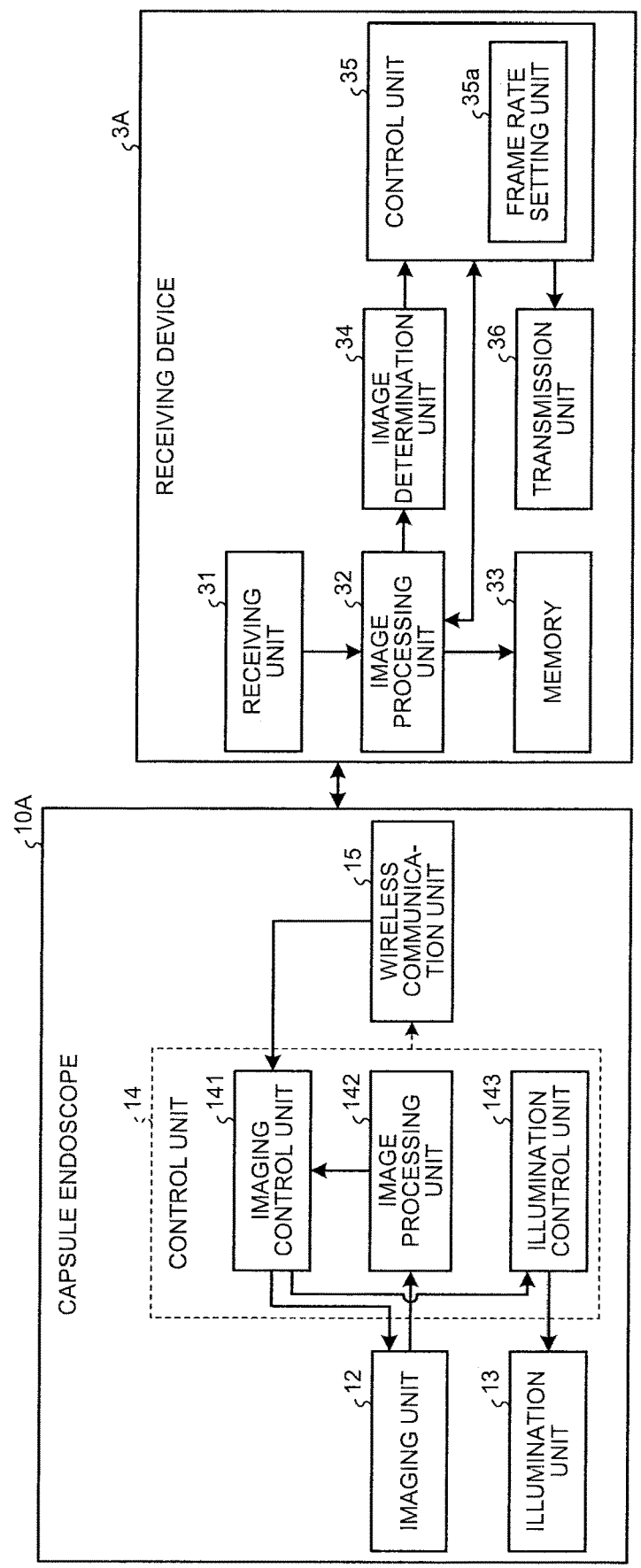
FIG. 5 is a block diagram illustrating a configuration example of a capsule endoscope and a receiving device according to modification 1-1.

In the configuration described in the first embodiment, the image determination unit and the frame rate setting unit may also be provided in the receiving device 3 illustrated in FIG. 1. FIG. 5 is a block diagram illustrating a configuration example of a capsule endoscope and a receiving device according to modification 1-1. As illustrated in FIG. 5, a capsule endoscope 10A does not include the image determination unit and the frame rate setting unit. In contrast, a receiving device 3A includes a receiving unit 31 that receives, via the receiving antenna unit 4 (see FIG. 1), an image wirelessly transmitted from the capsule endoscope 10A; an image processing unit 32 that performs predetermined image processing on the image received by the receiving unit 31; a memory 33 that stores therein the image subjected to the image processing; an image determination unit 34 that determines whether the image is useful for observation; a control unit 35 that controls an operation of each of the units and that generates, based on the determination result determined by the image determination unit 34, control information that is used to change an imaging frame rate in the imaging unit 12; and a transmission unit 36 that transmits various kinds of instruction information including the control information generated by the control unit 35 to the capsule endoscope 10A.

The control unit 35 includes a frame rate setting unit 35a that sets an imaging frame rate based on the number of images (bubble residue images) that are not useful for observation determined by the image determination unit 34. Then, the control unit 35 generates, based on the imaging frame rate set by the frame rate setting unit 35a, the control information that is used to change the imaging frame rate in the imaging unit 12.

According to modification 1-1, by reducing an amount of processes performed in the capsule endoscope 10A, it is possible to further suppress consumption of the battery in the capsule endoscope 10A.

Furthermore, in the first embodiment, a description has been given of the configuration having the frame rate setting unit; however, the configuration is not limited to this. For example, it may also be possible to use the configuration in which the imaging control unit 141 does not include the frame rate setting unit and decreases, if it is determined by the image determination unit 144 that the image captured by the imaging unit 12 is a bubble residue image, the imaging frame rate in the imaging unit 12.

Furthermore, it may also be possible to use the configuration in which the capsule endoscope includes the image determination unit and the receiving device includes the frame rate setting unit, or, alternatively, the receiving device includes the image determination unit and the capsule endoscope includes the frame rate setting unit.

Second Embodiment

Figure 6:
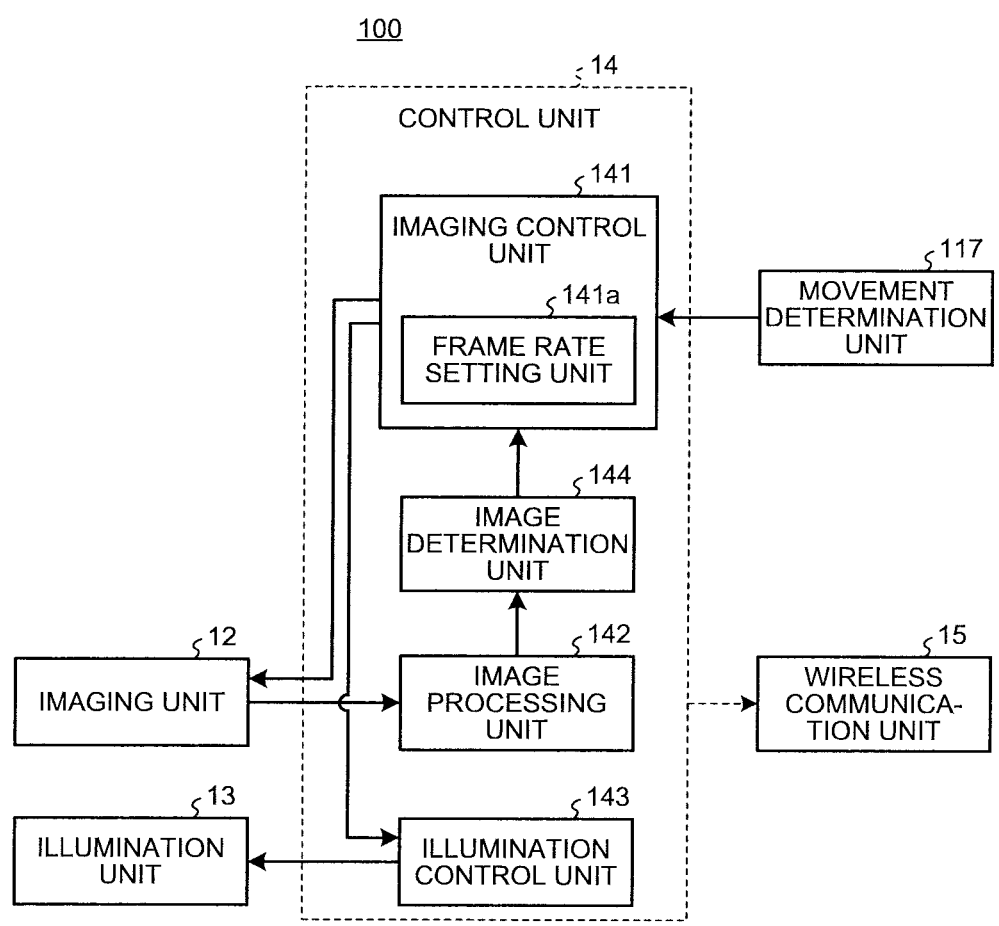
FIG. 6 is a block diagram illustrating a configuration of a capsule endoscope according to a second embodiment.

FIG. 6 is a block diagram illustrating a configuration of a capsule endoscope according to a second embodiment. As illustrated in FIG. 6, a capsule endoscope 100 includes a movement determination unit 117 that determines the magnitude of movement of the capsule endoscope 100. The configuration other than this is the same as that described in the first embodiment; therefore, descriptions thereof will appropriately be omitted.

The movement determination unit 117 is formed by, for example, an acceleration sensor and a processor, such as a CPU. The movement determination unit 117 determines the magnitude of the movement of the capsule endoscope 100 based on acceleration information on the capsule endoscope 100 detected by the acceleration sensor. Specifically, the movement determination unit 117 determines whether the magnitude of the movement of the capsule endoscope 100 is smaller than a predetermined amount.

Furthermore, if one or the predetermined number of images (bubble residue images) that are not useful for observation determined by the image determination unit 144 continue and if the movement determination unit 117 determines that the magnitude of the movement of the capsule endoscope 100 is smaller than the predetermined amount, the frame rate setting unit 141a sets the imaging frame rate to be decreased.

Figure 7:
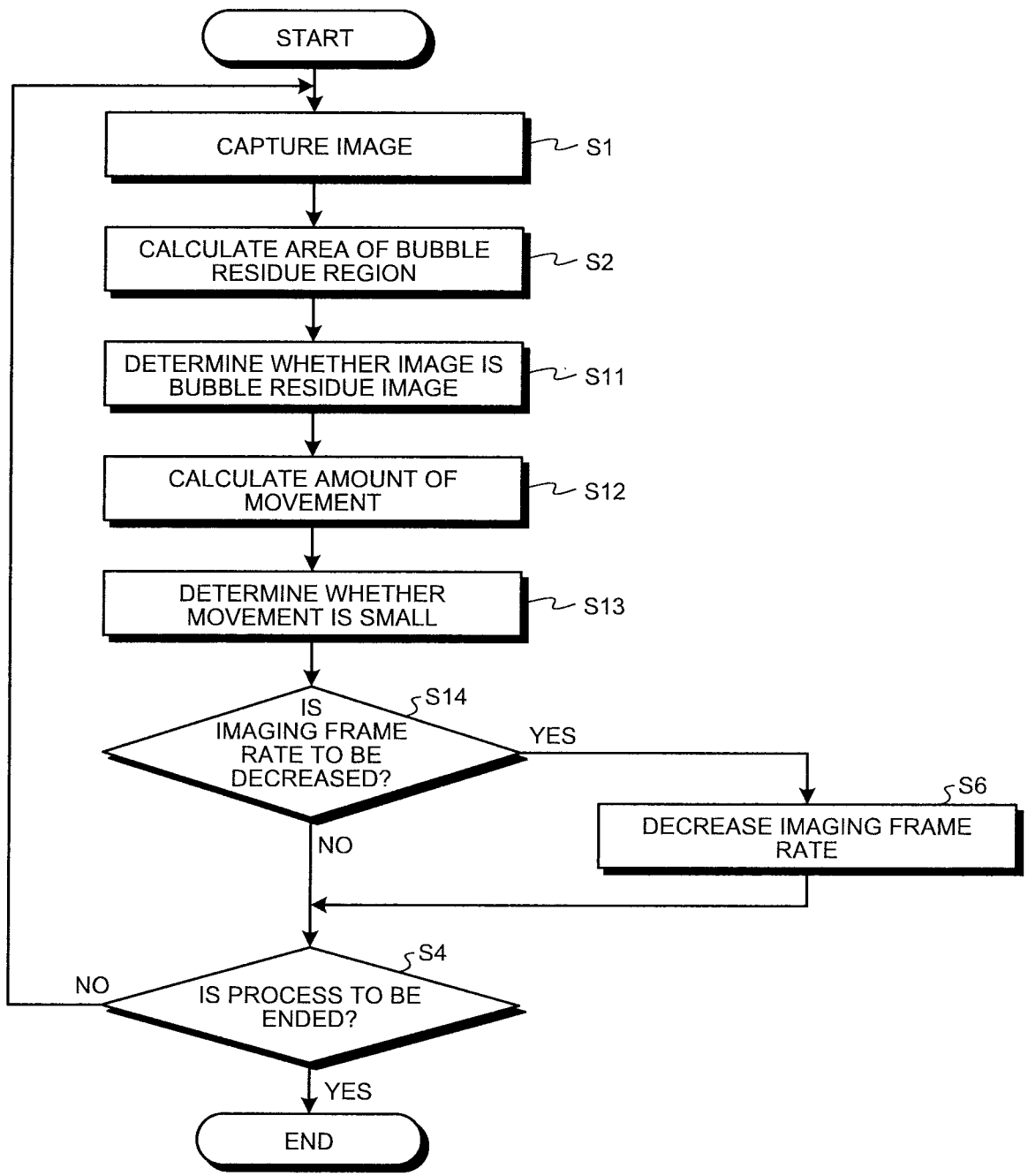
FIG. 7 is a flowchart illustrating the flow of an operation of the capsule endoscope according to the second embodiment.

In the following, an operation performed in the capsule endoscope 100 will be described. FIG. 7 is a flowchart illustrating the flow of an operation of the capsule endoscope according to the second embodiment. As illustrated in FIG. 7, first, similarly to the first embodiment, processes at Steps S1 and S2 are performed.

Subsequently, the image determination unit 144 determines whether the area of the region in which a bubble or a residue is imaged in the image is a bubble residue image having an amount equal to or greater than a predetermined amount (Step S11).

Then, the movement determination unit 117 calculates, based on the acceleration information on the capsule endoscope 100 detected by the acceleration sensor, an amount of the movement of the capsule endoscope 100 (Step S12). Furthermore, the movement determination unit 117 determines whether the movement of the capsule endoscope 100 is smaller than the predetermined amount (Step S13).

Here, the frame rate setting unit 141a determines whether the imaging frame rate in the imaging unit 12 is to be decreased (Step S14). FIG. 8 is a diagram illustrating a condition for setting, by a frame rate setting unit, an imaging frame rate based on determination results obtained by an image determination unit and a movement determination unit. As illustrated in FIG. 8, if the image determination unit 144 determines that the image is a bubble residue image and if the movement determination unit 117 determines that the magnitude of the movement of the capsule endoscope 100 is smaller than the predetermined amount, the frame rate setting unit 141a sets the imaging frame rate to be decreased and sets, in a case other than this, the imaging frame rate to be maintained.

If the frame rate setting unit 141a sets the imaging frame rate to be decreased (Yes at Step S14), the imaging control unit 141 decreases the imaging frame rate in the imaging unit 12 based on the setting performed by the frame rate setting unit 141a (Step S6). Thereafter, it is determined whether the process at Step S4 is to be ended and then the process is continued or ended.

In contrast, if the frame rate setting unit 141a sets the imaging frame rate to be maintained (No at Step S14), it is determined whether the process at Step S4 is to be ended and then the process is continued or ended.

As described above, according to the second embodiment, if the capsule endoscope 100 is located at the position in which an image that is useful for observation is not able to be captured due to a lot of bubbles or residues and if the movement of the capsule endoscope 100 is small, the imaging frame rate in the imaging unit 12 is automatically decreased. Consequently, the capsule endoscope 100 can suppress consumption of a battery and suppress capturing of an image that is not useful for observation.

Modification 2-1

Figure 9:
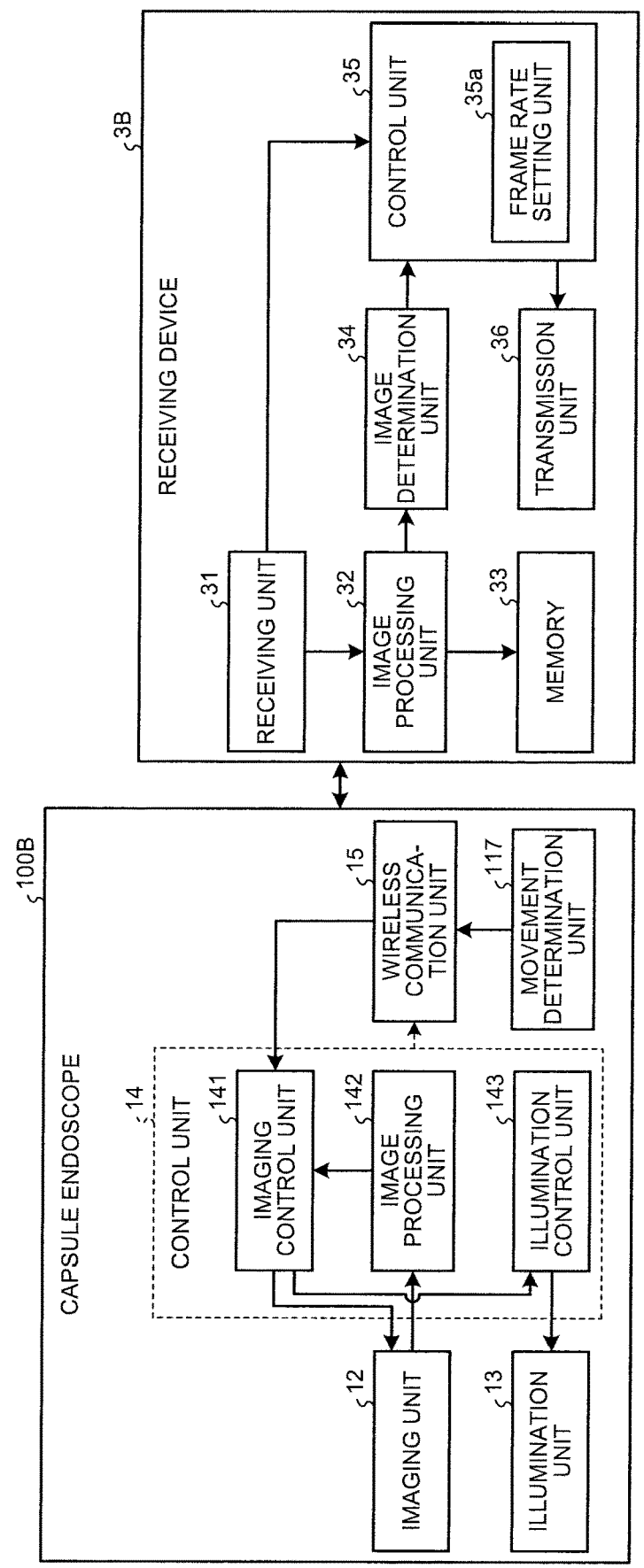
FIG. 9 is a block diagram illustrating a configuration example of a capsule endoscope and a receiving device according to modification 2-1.

In the configuration described in the second embodiment, the image determination unit and the frame rate setting unit may also be provided in the receiving device 3 illustrated in FIG. 1. FIG. 9 is a block diagram illustrating a configuration example of a capsule endoscope and a receiving device according to modification 2-1. As illustrated in FIG. 9, a capsule endoscope 100B includes the movement determination unit 117 but does not include the image determination unit and the frame rate setting unit. In contrast, a receiving device 3B includes the receiving unit 31 that receives, via the receiving antenna unit 4 (see FIG. 1), the image wirelessly transmitted from the capsule endoscope 100B and the information related to the magnitude of the movement of the capsule endoscope 100B determined by the movement determination unit 117; the image processing unit 32 that performs predetermined image processing on the image received by the receiving unit 31; the memory 33 that stores therein the image subjected to the image processing; the image determination unit 34 that determines whether the image is useful for observation; the control unit 35 that controls an operation of each of the units and that generates, based on the determination result determined by the image determination unit 34, control information that is used to change an imaging frame rate in the imaging unit 12; and the transmission unit 36 that transmits various kinds of instruction information including the control information generated by the control unit 35 to the capsule endoscope 100B.

The control unit 35 includes the frame rate setting unit 35a that sets an imaging frame rate based on the number of images (bubble residue images) that are not useful for observation determined by the image determination unit 34 and based on the information related to the magnitude of the movement of the capsule endoscope 100B received by the receiving unit 31. Then, the control unit 35 generates, based on the imaging frame rate set by the frame rate setting unit 35a, the control information that is used to change the imaging frame rate in the imaging unit 12.

Furthermore, it may also be possible to use the configuration in which the capsule endoscope includes the image determination unit and the receiving device includes the frame rate setting unit, or, alternatively, the receiving device includes the image determination unit and the capsule endoscope includes the frame rate setting unit.

Modification 2-2

Figure 10:
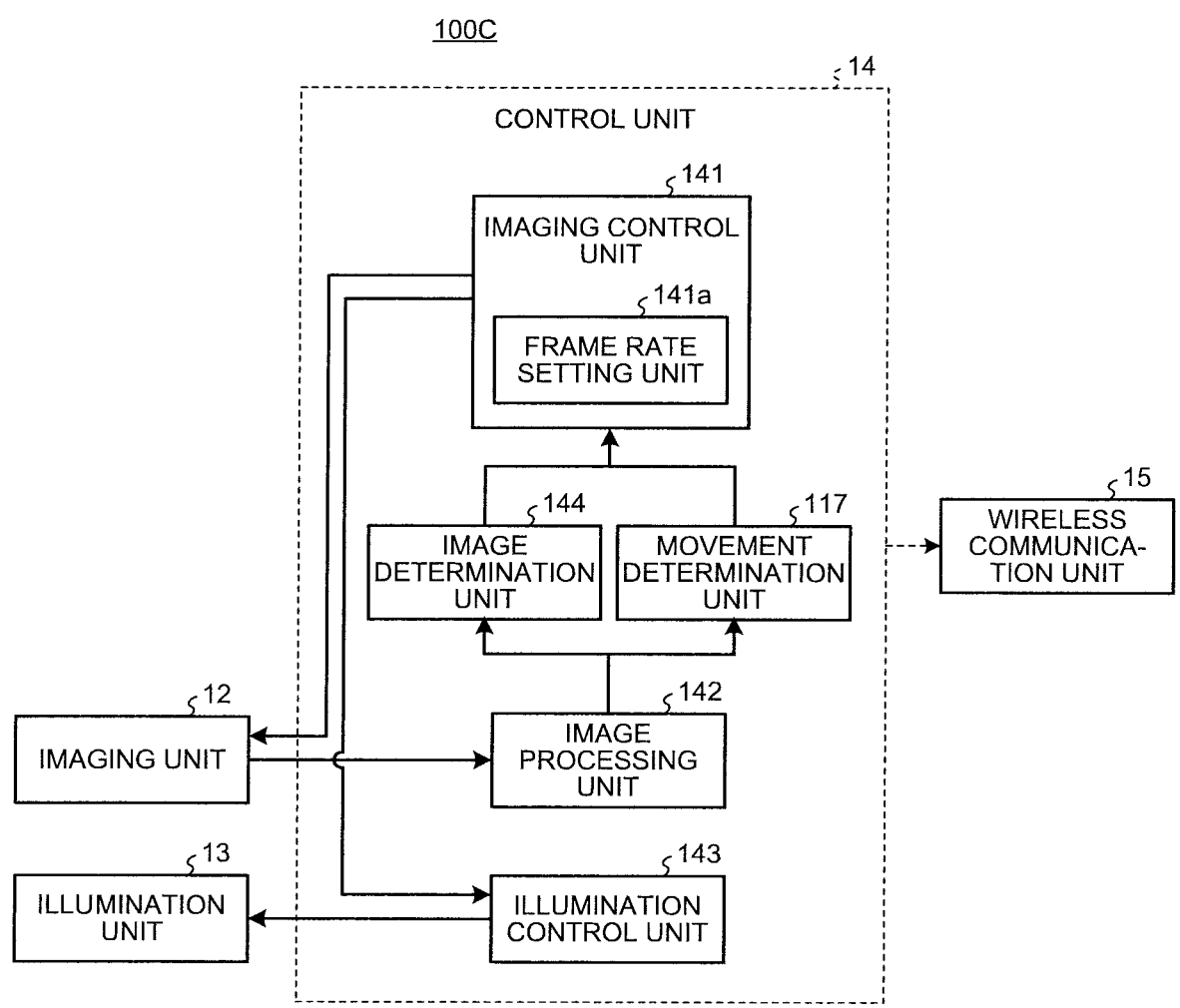
FIG. 10 is a block diagram illustrating a configuration example of a capsule endoscope and a receiving device according to modification 2-2.

In the configuration described in the second embodiment, determination of the magnitude of the movement of a capsule endoscope 100C may also be performed by using the image captured by the imaging unit 12. FIG. 10 is a block diagram illustrating a configuration example of a capsule endoscope and a receiving device according to modification 2-2. As illustrated in FIG. 10, the movement determination unit 117 performs determination of the magnitude of the movement of the capsule endoscope 100C by using an image group acquired from the image processing unit 142. Specifically, the movement determination unit 117 compares previous and subsequent images arranged in a time series and determines, if a change between the images is large, that the magnitude of the movement of the capsule endoscope 100C is large. The movement determination unit 117 may also determine the magnitude of the movement of the capsule endoscope 100C based on the degree of similarity of the previous and subsequent images or, alternatively, determine the magnitude of the movement of the capsule endoscope 100C by calculating a motion vector by comparing the previous and subsequent images.

Modification 2-3

Figure 11:
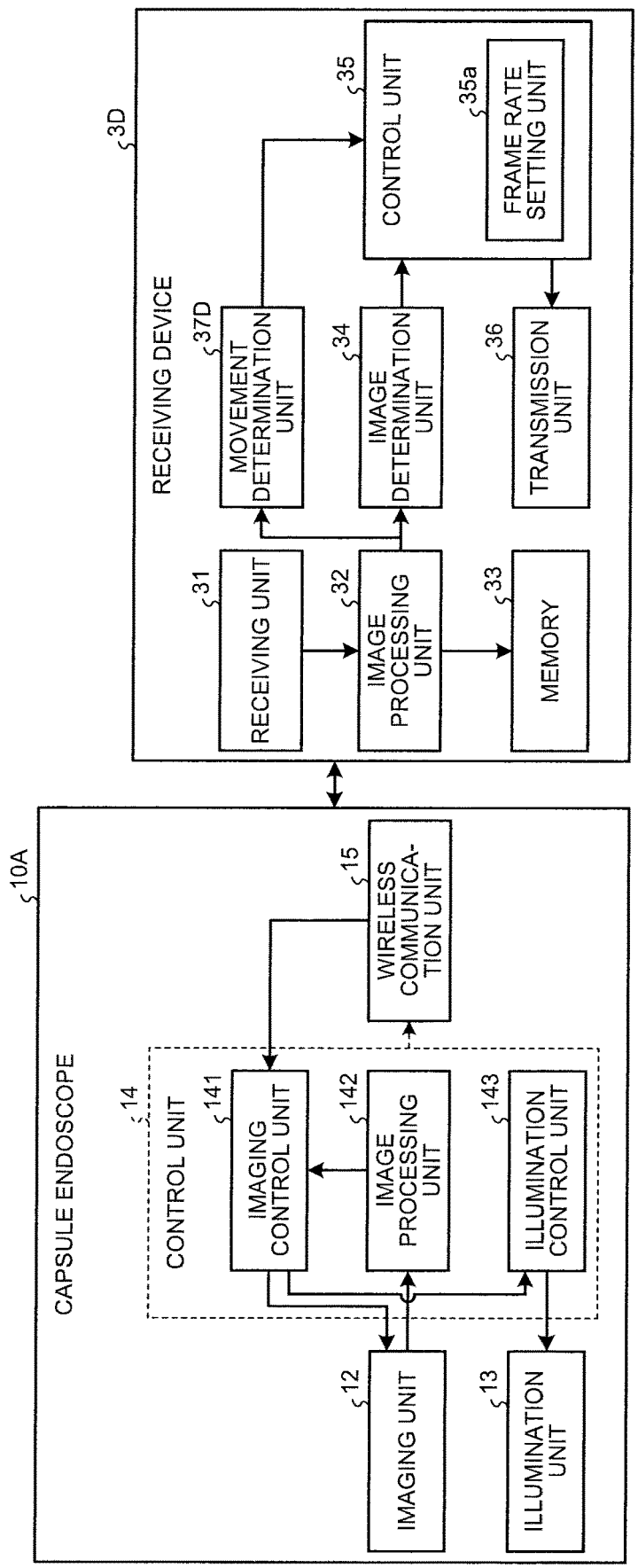
FIG. 11 is a block diagram illustrating a configuration example of a capsule endoscope and a receiving device according to modification 2-3.

Similarly to modification 2-2, when determination of the magnitude of the movement of the capsule endoscope is performed by an image captured by the imaging unit, it may also be possible to provide the image determination unit, the frame rate setting unit, and the movement determination unit in the receiving device 3 illustrated in FIG. 1. FIG. 11 is a block diagram illustrating a configuration example of a capsule endoscope and a receiving device according to modification 2-3. As illustrated in FIG. 11, similarly to modification 1-1 described with reference to FIG. 5, the capsule endoscope 10A does not include the image determination unit, the frame rate setting unit, and the movement determination unit. In contrast, a receiving device 3D includes the receiving unit 31 that receives, via the receiving antenna unit 4 (see FIG. 1), the image wirelessly transmitted from the capsule endoscope 10A; the image processing unit 32 that performs predetermined image processing on the image received by the receiving unit 31; a memory 33 that stores therein the image subjected to the image processing; the image determination unit 34 that determines whether the image is useful for observation; a movement determination unit 37D that determines the magnitude of the movement of the capsule endoscope 10A by using the image group acquired by the receiving unit 31; the control unit 35 that controls an operation of each of the units and that generates, based on the determination result determined by the image determination unit 34, control information that is used to change an imaging frame rate in the imaging unit 12; and the transmission unit 36 that transmits various kinds of instruction information including the control information generated by the control unit 35 to the capsule endoscope 10A.

The control unit 35 includes the frame rate setting unit 35a that sets an imaging frame rate based on the number of images (bubble residue images) that are not useful for observation determined by the image determination unit 34 and based on the magnitude of the movement of the capsule endoscope 10A determined by the movement determination unit 37D. Then, the control unit 35 generates, based on the imaging frame rate set by the frame rate setting unit 35a, the control information that is used to change the imaging frame rate in the imaging unit 12.

Furthermore, it may also be possible to provide, in the capsule endoscope, one of or a plurality of image determination units, movement determination units, and frame rate setting units.

Third Embodiment

The configuration of a capsule endoscope according to a third embodiment is the same as that of the capsule endoscope 100 according to the second embodiment described with reference to FIG. 6; therefore, descriptions thereof will appropriately be omitted.

The movement determination unit 117 determines the magnitude of the movement of the capsule endoscope 100 is smaller than the predetermined amount. The image determination unit 144 determines whether the image that has been subjected to image processing performed by the image processing unit 142 is useful for observation. If the image processing unit 142 determines that the image (bubble residue image) is not useful for observation or if the movement determination unit 117 determines that the magnitude of the movement of the capsule endoscope 100 is smaller than the predetermined amount, the frame rate setting unit 141a sets the imaging frame rate to be decreased.

Figure 12:
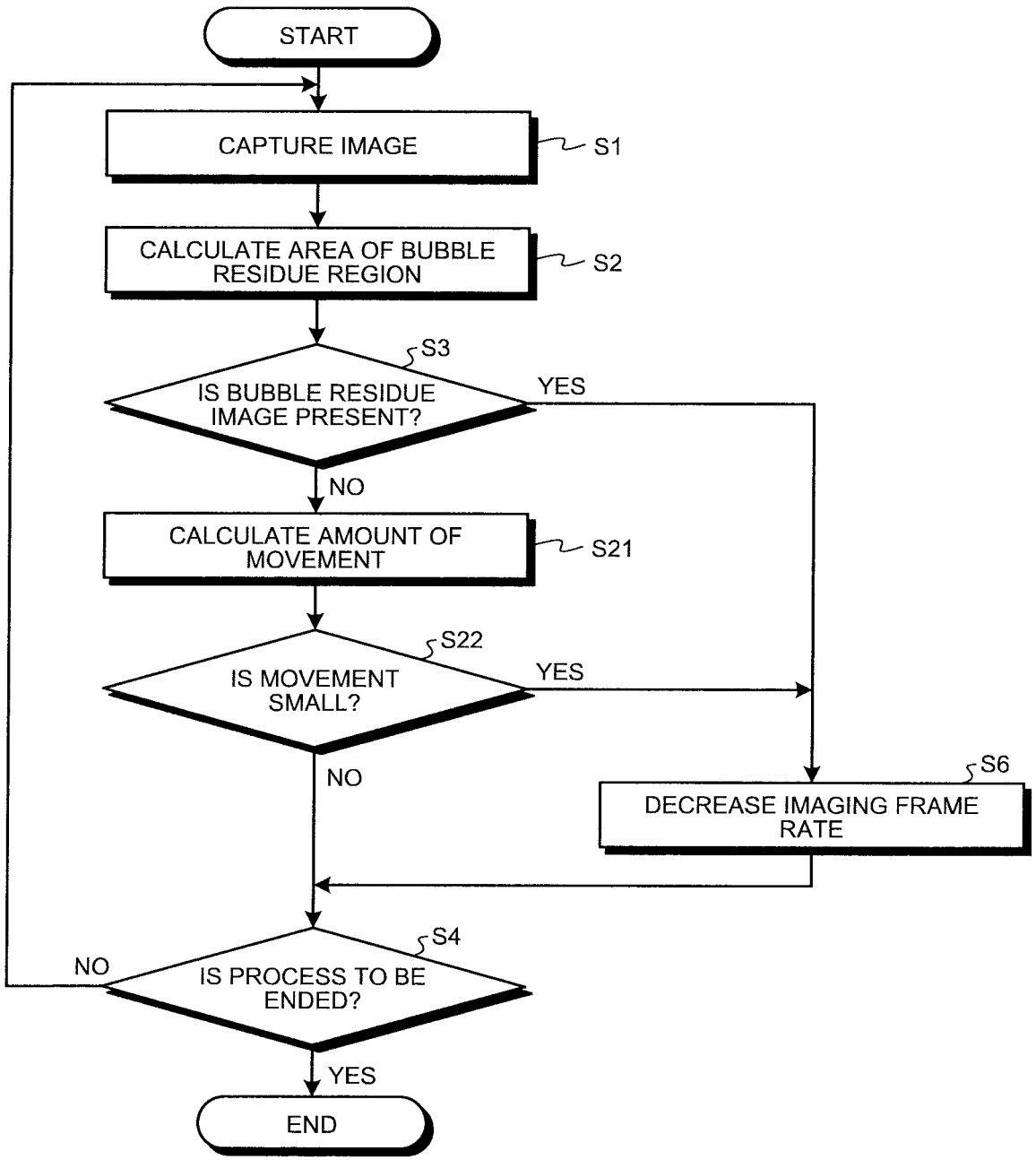
FIG. 12 is a flowchart illustrating the flow of an operation of a capsule endoscope according to a third embodiment.

In the following, an operation of the capsule endoscope 100 will be described. FIG. 12 is a flowchart illustrating the flow of an operation of a capsule endoscope according to a third embodiment. As illustrated in FIG. 12, first, similarly to the first embodiment, processes at Steps S1 and S2 are performed.

Furthermore, the image determination unit 144 determines whether the area of the region in which a bubble or a residue is imaged in the image is a bubble residue image having an amount equal to or greater than a predetermined amount (Step S3).

If the image determination unit 144 determines that the image is not the bubble residue image (No at Step S3), the movement determination unit 117 calculates an amount of the movement of the capsule endoscope 100 based on the acceleration information on the capsule endoscope 100 detected by the acceleration sensor (Step S21). Furthermore, the movement determination unit 117 determines whether the magnitude of the movement of the capsule endoscope 100 is smaller than the predetermined amount (Step S22).

If the movement determination unit 117 determines that the magnitude of the movement of the capsule endoscope 100 is greater than the predetermined amount (No at Step S22), it is determined whether the process at Step S4 is to be ended and then the process is continued or ended.

At Step S3, if the image determination unit 144 determines that the image is a bubble residue image (Yes at Step S3), the frame rate setting unit 141a sets the imaging frame rate in the imaging unit 12 to be decreased (Step S6). Thereafter, it is determined whether the process at Step S4 is to be ended and then the process is continued or ended.

Furthermore, at Step S22, if the movement determination unit 117 determines that the magnitude of the movement of the capsule endoscope 100 is smaller than the predetermined (Yes at Step S22), the frame rate setting unit 141a sets the imaging frame rate in the imaging unit 12 to be decreased (Step S6). Thereafter, it is determined whether the process at Step S4 is to be ended and then the process is continued or ended.

As described above, according to the third embodiment, if the capsule endoscope 100 is located at the position in which an image that is useful for observation is not able to be captured due to a lot of bubbles or residues, the imaging frame rate in the imaging unit 12 is automatically decreased. Furthermore, according to the third embodiment, even when the image captured by the imaging unit 12 is not a bubble residue image, if the magnitude of the movement of the capsule endoscope 100 is small, the imaging frame rate in the imaging unit 12 is automatically decreased. Consequently, the capsule endoscope 100 can suppress consumption of a battery and suppress capturing of an image that is not useful for observation and can prevent the images at the same position from being captured number of times even if the images are useful for observation.

Fourth Embodiment

The configuration of a capsule endoscope according to a fourth embodiment is the same as that of the capsule endoscope 100 according to the second embodiment described with reference to FIG. 6; therefore, descriptions thereof will be omitted.

The movement determination unit 117 determines the magnitude of the movement of the capsule endoscope 100. The frame rate setting unit 141a sets the imaging frame rate to be continuously or gradually decreased by a larger amount as the number of images (bubble residue images) that are not useful for observation determined by the image determination unit 144 is greater and sets the imaging frame rate to be continuously or gradually decreased by a larger amount as the magnitude of the movement of the capsule endoscope 100 determined by the movement determination unit 117 is smaller.

Figure 13:
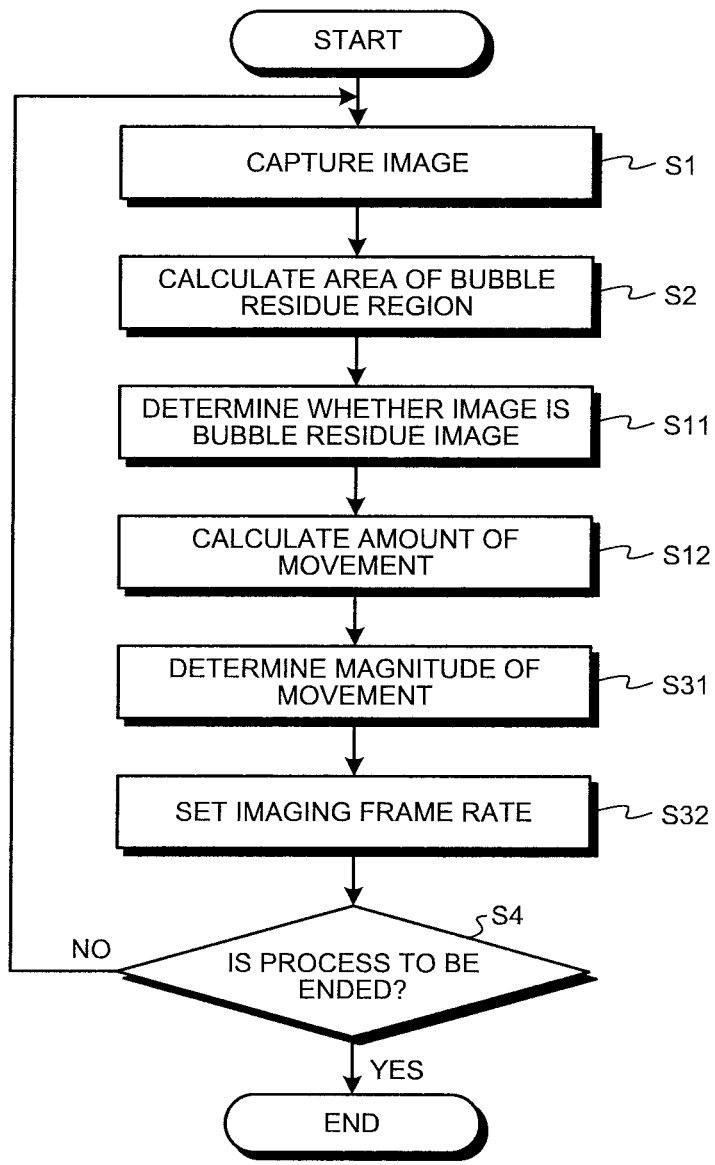
FIG. 13 is a flowchart illustrating the flow of an operation of a capsule endoscope according to a fourth embodiment.

In the following, an operation of the capsule endoscope 100 will be described. FIG. 13 is a flowchart illustrating the flow of an operation of a capsule endoscope according to a fourth embodiment. As illustrated in FIG. 13, first, similarly to the first embodiment, processes at Steps S1 and S2 are performed. Furthermore, similarly to the second embodiment, processes at Steps S11 and S12 are performed.

Subsequently, the movement determination unit 117 determines the magnitude of the movement of the capsule endoscope 100 (Step S31).

Figure 14:
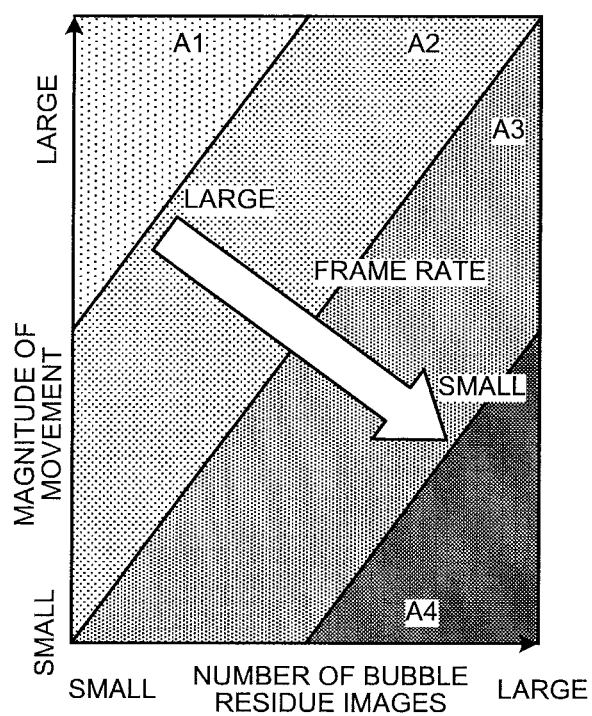
FIG. 14 is a diagram illustrating an association relationship among the number of bubble residue images, an amount of movement of the capsule endoscope, and an imaging frame rate set by the frame rate setting unit.

Then, based on the number of bubble residue images determined by the image determination unit 144 and based on the magnitude of the movement of the capsule endoscope 100 determined by the movement determination unit 117, the frame rate setting unit 141a sets the imaging frame rate to be gradually changed (Step S32). FIG. 14 is a diagram illustrating an association relationship among the number of bubble residue images, an amount of movement of the capsule endoscope, and an imaging frame rate set by the frame rate setting unit. As illustrated in FIG. 14, the frame rate setting unit 141a sets the imaging frame rate in the imaging unit 12 to be decreased by a larger amount as the number of bubble residue images included in the predetermined number of images (for example, immediately previous 10 images) is greater and sets the imaging frame rate to be decreased by a larger amount as the magnitude of the movement of the capsule endoscope 100 determined by the movement determination unit 117 is smaller. FIG. 14 illustrates an example of the imaging frame rate that can be changed at four levels of A1 to A4 (A1>A2>A3>A4);

however, the imaging frame rate may also be changed at multiple levels greater than four or may also be continuously changed. Thereafter, it is determined whether the process at Step S4 is to be ended and then the process is continued or ended.

As described above, according to the fourth embodiment, the imaging frame rate is automatically decreased as the number of bubbles or residues located at the position of the capsule endoscope 100 is greater, whereas the imaging frame rate is automatically decreased as the movement of the capsule endoscope 100 is smaller. Consequently, the capsule endoscope 100 can suppress consumption of a battery and suppress capturing of an image that is not useful for observation.

Fifth Embodiment

Figure 15:
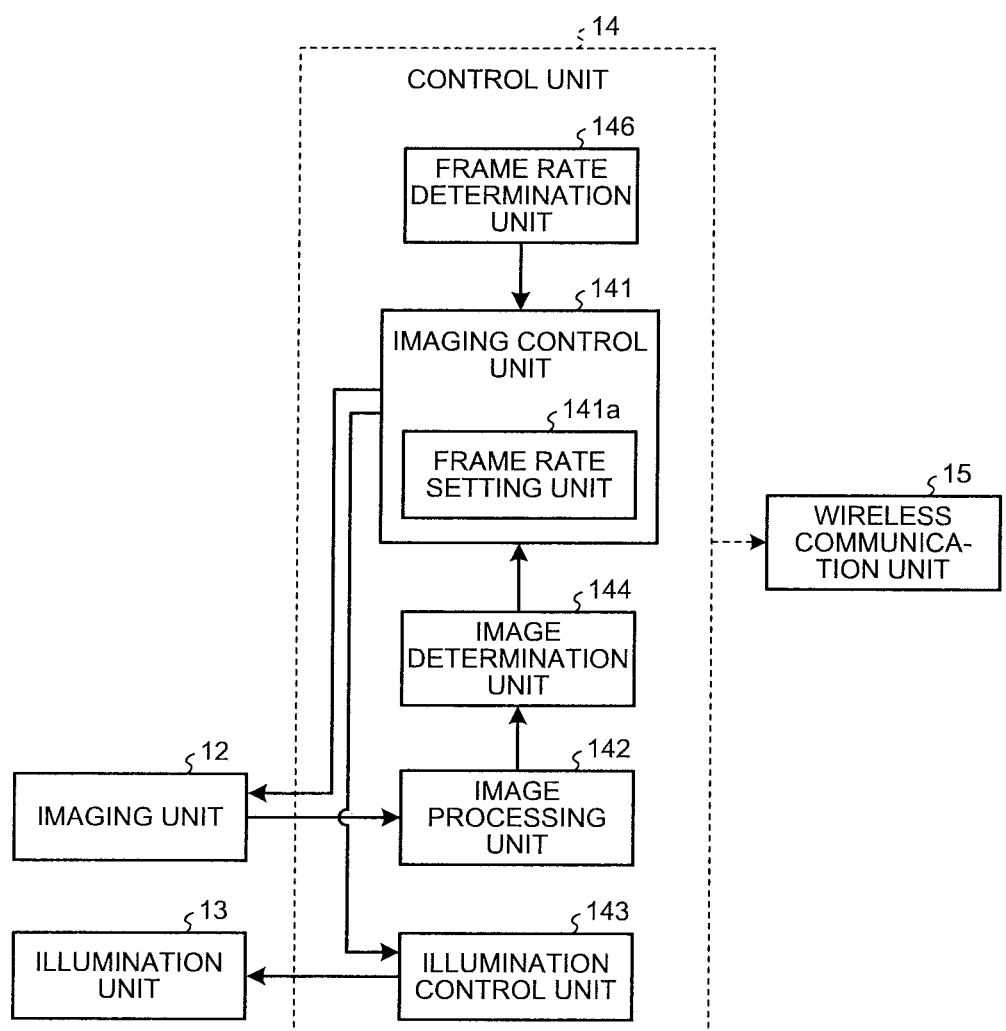
FIG. 15 is a block diagram illustrating a configuration of a capsule endoscope according to a fifth embodiment.

FIG. 15 is a block diagram illustrating a configuration of a capsule endoscope according to a fifth embodiment. As illustrated in FIG. 15, a capsule endoscope 200 includes a frame rate determination unit 146 that determines the state of the imaging frame rate in the imaging unit 12. The configuration other than this is the same as that described in the first embodiment; therefore, descriptions thereof will appropriately be omitted.

If the frame rate determination unit 146 determines that the state of imaging frame rate is lower than the normal state, the image determination unit 144 determines whether a plurality of images captured by the imaging unit 12 is the images (bubble residue images) that are not useful for observation. If the number of images (bubble residue images) that are determined by the image determination unit 144 that the images are not useful for observation is equal to or greater than a predetermined number, the frame rate setting unit 141a sets the imaging frame rate so as to maintain the state dropped from the normal state.

The frame rate determination unit 146 is constituted by, for example, a processor, such as a CPU, as a part of the control unit 14 but may also be constituted by a CPU that is different from the control unit 14.

Figure 16:
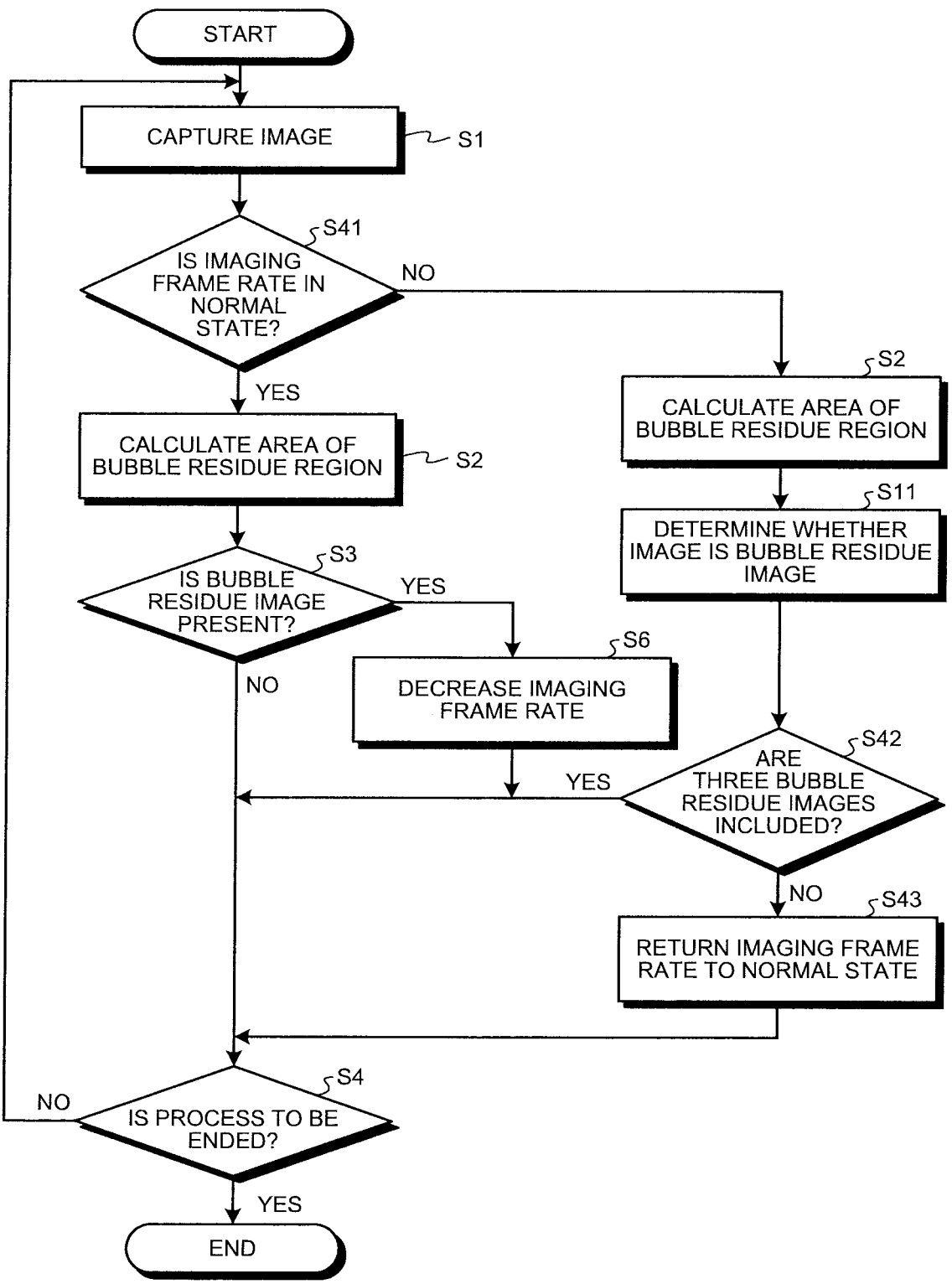
FIG. 16 is a flowchart illustrating the flow of an operation of the capsule endoscope according to the fifth embodiment.
Figure 17:
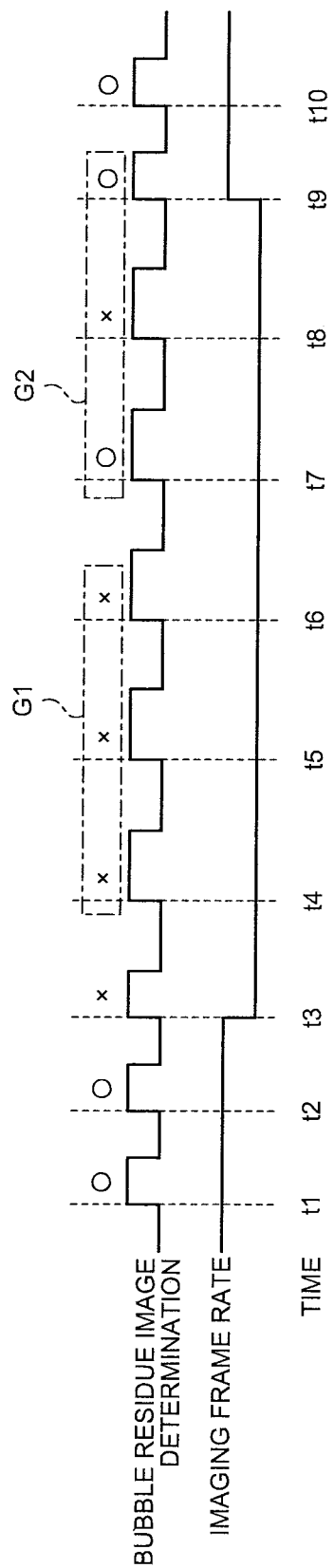
FIG. 17 is a timing chart illustrating an operation of the capsule endoscope according to the fifth embodiment.

In the following, an operation of the capsule endoscope 200 will be described. FIG. 16 is a flowchart illustrating the flow of an operation of the capsule endoscope according to the fifth embodiment. FIG. 17 is a timing chart illustrating an operation of the capsule endoscope according to the fifth embodiment. As illustrated in FIG. 16, first, similarly to the first embodiment, the process at Step S1 is performed.

Subsequently, the frame rate determination unit 146 determines whether the imaging frame rate in the imaging unit 12 is in the normal state (Step S41).

As indicated by time t1 to t3 illustrated in FIG. 17, if the frame rate determination unit 146 determines that the imaging frame rate is in the normal state (high state) (Yes at Step S41), similarly to the first embodiment, the processes at Steps S2, 3, 4, and 6 are appropriately performed. Here, if the images captured by the imaging unit 12 are not bubble residue images (time t1 and t2), the frame rate setting unit 141a sets the imaging frame rate in the imaging unit 12 so as to maintain in the normal state. In contrast, if the image captured by the imaging unit 12 is a bubble residue image (time t3), the frame rate setting unit 141a sets the imaging frame rate in the imaging unit 12 to be decreased. Then, the imaging control unit 141 decreases the imaging frame rate in the imaging unit 12 based on the setting received from the frame rate setting unit 141a (Step S6).

In contrast, at Step S41, if the frame rate determination unit 146 determines that the imaging frame rate is not in the normal state (low state) (No at Step S41), the image determination unit 144 performs, similarly to the first embodiment, the process at Step S2 and then determines whether the plurality of images (for example, three images) captured by the imaging unit 12 is a bubble residue image (Step S11). Thereafter, the frame rate setting unit 141a determines, from among the three images that are determined by the image determination unit 144 whether the images are bubble residue images, whether the number of images determined to be the bubble residue images is equal to or greater than the predetermined number (for example, three images) (Step S42). Furthermore, here, an example in which the processes at Step S2 to Step S42 is performed one time every three frames; however, the processes may also be performed every single frame.

If the frame rate setting unit 141a determines that three bubble residue images are included (Yes at Step S42, a group G1 illustrated in FIG. 17), the frame rate setting unit 141a sets the imaging frame rate in the imaging unit 12 so as to maintain in the state dropped from the normal state. Thereafter, it is determined whether the process at Step S4 is to be ended and then the process is continued or ended.

In contrast, if the frame rate setting unit 141a determines that the three or more bubble residue images are not included (No at Step S42, a group G2 illustrated in FIG. 17), the frame rate setting unit 141a sets the imaging frame rate in the imaging unit 12 to be returned to the normal state (set to high). Then, the imaging control unit 141 returns the imaging frame rate of the imaging unit 12 to the normal state based on the setting of the frame rate setting unit 141a (Step S43). Thereafter, it is determined whether the process at Step S4 is to be ended and then the process is continued or ended.

As described above, according to the fifth embodiment, if the capsule endoscope 200 is located at the position in which an image that is useful for observation is not able to be captured due to a lot of bubbles or residues, the imaging frame rate in the imaging unit 12 is automatically decreased and, if this state is resolved, the imaging frame rate in the imaging unit 12 is automatically returned to the normal state (set to high). Consequently, the capsule endoscope 200 can suppress consumption of a battery and suppress capturing of an image that is not useful for observation.

Sixth Embodiment

The configuration of a capsule endoscope according to the sixth embodiment is the same as that of the capsule endoscope 10 described in the first embodiment with reference to FIG. 3; therefore, descriptions thereof will appropriately be omitted.

The frame rate setting unit 141a sets the imaging frame rate to be continuously or gradually decreased by a larger amount as the number of continuous images that have been determined by the image determination unit 144 that the images (bubble residue images) are not useful for observation is greater. The number of continuous images is, for example, the number of times the image that is not useful for observation continues; however, it may also be continuous time for which an image that is not useful for observation continues or may also be a continued distance of the continuous image.

Figure 18:
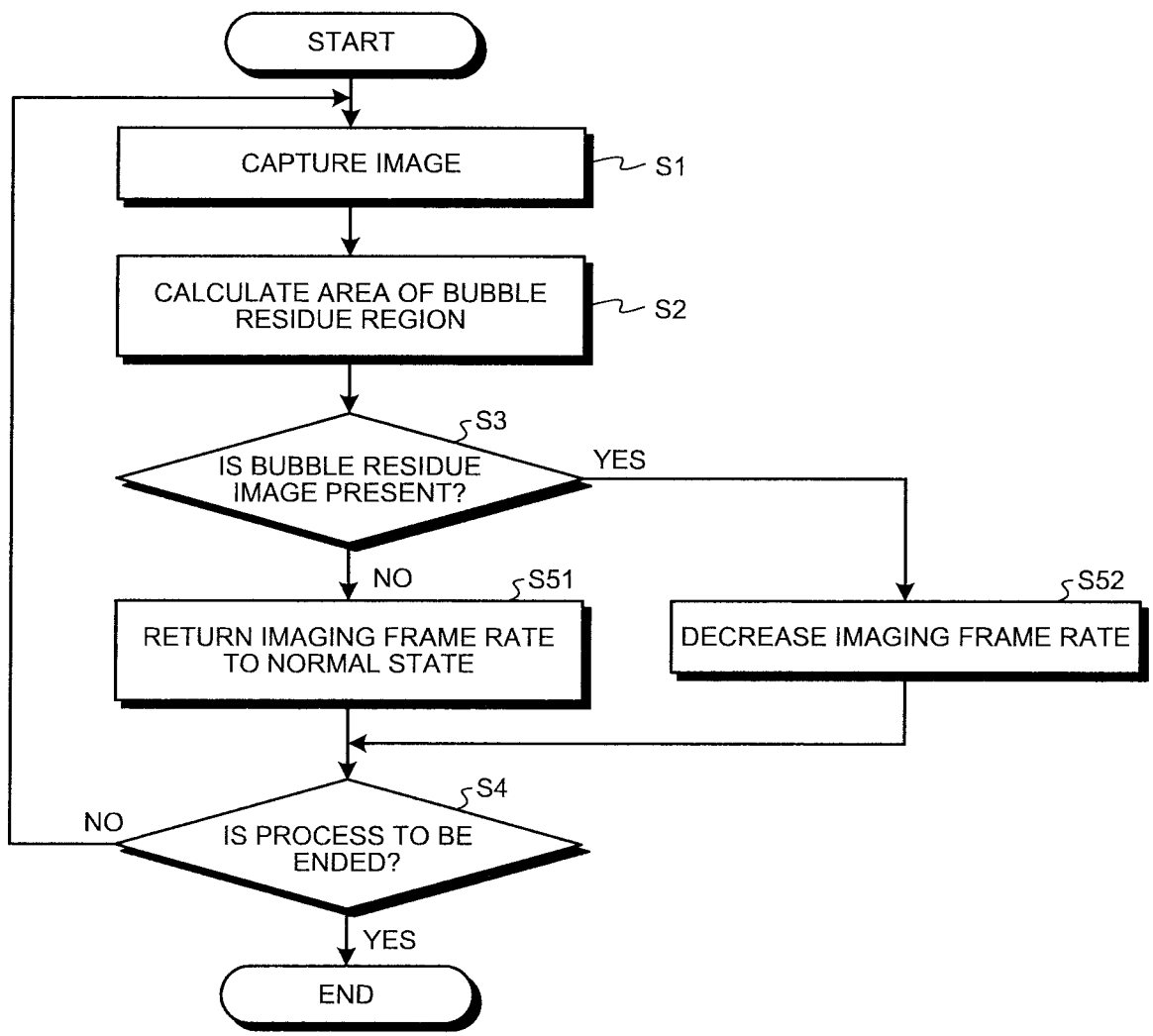
FIG. 18 is a flowchart illustrating the flow of an operation of the capsule endoscope according to a sixth embodiment.

In the following, an operation of the capsule endoscope 10 will be described. FIG. 18 is a flowchart illustrating the flow of an operation of the capsule endoscope according to a sixth embodiment. As illustrated in FIG. 18, first, similarly to the first embodiment, the processes at Steps S1 and S2 are performed.

Furthermore, the image determination unit 144 determines whether the image is a bubble residue image in which the area of the region having a bubble or a residue imaged in the image is an amount equal or greater than a predetermined amount (Step S3).

If the image determination unit 144 determines that the image is not a bubble residue image (No at Step S3), the frame rate setting unit 141*a* sets the imaging frame rate in the imaging unit 12 to be returned to the normal state (set to high). Then, the imaging control unit 141 returns, based on the setting of the frame rate setting unit 141*a*, the imaging frame rate in the imaging unit 12 to the normal state (Step S51).

In contrast, if the image determination unit 144 determines that the image is a bubble residue image (Yes at Step S3), the frame rate setting unit 141*a* sets the imaging frame rate in the imaging unit 12 to be decreased. Then, the imaging control unit 141 decreases, based on the setting of the frame rate setting unit 141*a*, the imaging frame rate in the imaging unit 12 (Step S52). Thereafter, it is determined whether the process at Step S4 is to be ended and then the process is continued or ended.

Here, at Step S52, if the image determination unit 144 continuously determines that the images captured by the imaging unit 12 are bubble residue images, the frame rate setting unit 141*a* sets the imaging frame rate in the imaging unit 12 to continuously or gradually be decreased by a larger amount. Specifically, if two bubble residue images continue, the frame rate setting unit 141*a* sets the imaging frame rate to be decreased by two levels and sets, if three bubble residue images continue, the imaging frame rate to be decreased by three levels. The number of levels for decreasing the imaging frame rate may also be any level and a lower limit may also be set such that the imaging frame rate is not below the lower limit.

As described above, according to the sixth embodiment, if the capsule endoscope 10 is located at the position in which an image that is useful for observation is not able to be captured due to a lot of bubbles or residues, the imaging frame rate in the imaging unit 12 is automatically and gradually decreased. Consequently, the capsule endoscope 10 can suppress consumption of a battery and suppress capturing of an image that is not useful for observation.

According to the present disclosure, it is possible to implement a capsule endoscope, a receiving device, an operation method of the capsule endoscope, and an operation program of the capsule endoscope that can suppress needless consumption of a battery and suppress capturing of an image that is not useful for observation.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope comprising:
    an image sensor configured to generate images by capturing an inside of a subject at an imaging frame rate that is variable; and
    a processor comprising hardware, the processor being configured to:
        determine whether any of the images is a first image whose feature amount related to a region having a bubble or a residue imaged is equal to or greater than a predetermined amount,
        determine whether the images that have been determined to be the first image continue a predetermined number of times, set the imaging frame rate based on a predetermined number of continuous images that have been determined to be the first image, and
        change the imaging frame rate in the image sensor to the set imaging frame rate.

2. The capsule endoscope according to claim 1, wherein the processor:
    determines a magnitude of movement of the capsule endoscope, and
    sets the imaging frame rate based on the number of the images that have been determined to be the first image and based on the magnitude of the movement of the capsule endoscope.

3. The capsule endoscope according to claim 1, wherein the processor decreases the imaging frame rate when the images that have been determined to be the first image continue predetermined times.

4. The capsule endoscope according to claim 2, wherein the processor decreases the imaging frame rate when the images that have been determined to be the first image continue predetermined times and when the magnitude of the movement of the capsule endoscope is smaller than a predetermined amount.

5. The capsule endoscope according to claim 1, wherein the processor continuously or gradually decreases the imaging frame rate by a larger amount as the number of the images that are continuous images that have been determined to be the first image increases.

6. The capsule endoscope according to claim 2, wherein the processor continuously or gradually decreases the imaging frame rate by a larger amount as the number of the images that have been determined to be the first image increases continuously or gradually decreases the imaging frame rate by a larger amount as the magnitude of the movement of the capsule endoscope decreases.

7. The capsule endoscope according to claim 1, wherein the processor:
    determines a state of the imaging frame rate,
    determines whether or not any of the images are the first image when the imaging frame rate has been determined to be decreased from the imaging frame rate in a normal state, and
    maintains the imaging frame rate to be decreased from the imaging frame rate in the normal state when the number of the images that have been determined to be the first image is equal to or greater than a predetermined number.

8. A receiving device comprising:
    a receiver configured to receive images from a capsule endoscope including an image sensor that generates the images by capturing an inside of a subject at an imaging frame rate that is variable;
    a processor comprising hardware, the processor being configured to:
        determine whether any of the images is a first image whose feature amount related to a region having a bubble or a residue imaged is equal to or greater than a predetermined amount,
        determine whether the images that have been determined to be the first image continue a predetermined number of times, set the imaging frame rate based on a predetermined number of continuous images that have been determined to be the first image, and generate control information related to control of the imaging frame rate and change the imaging frame rate in the image sensor to the set imaging frame rate; and a transmitter configured to transmit the control information to the capsule endoscope.

9. The receiving device according to claim 8, wherein the receiver receives, from the capsule endoscope, information related to a magnitude of movement of the capsule endoscope, and the processor sets the imaging frame rate based on the number of the images that have been determined to be the first image and based on the information related to the magnitude of the movement of the capsule endoscope.

10. The receiving device according to claim 8, wherein the processor:

determines a magnitude of the movement of the capsule endoscope, and sets the imaging frame rate based on the number of the images that have been determined to be the first image and based on the magnitude of the movement of the capsule endoscope.

11. An operation method of a capsule endoscope, the method comprising:

generating, by an image sensor, images by capturing an inside of a subject at an imaging frame rate that is variable;

determining, by a processor comprising hardware, whether any of the images is a first image whose feature amount related to a region having a bubble or a residue imaged is equal to or greater than a predetermined amount;

determining, by the processor, whether the images that have been determined to be the first image continue a predetermined number of times; setting, by the processor, the imaging frame rate based on a predetermined number of continuous images that have been determined to be the first image, and changing, by the processor, the imaging frame rate in the image sensor to the set imaging frame rate.

12. A non-transitory computer readable recording medium on which an executable program is recorded, the program instructing a processor of a capsule endoscope or a receiving device that receives images from the capsule endoscope to execute:

generating, by an image sensor, the images by capturing an inside of a subject at an imaging frame rate that is variable;

determining, by the processor comprising hardware, whether any of the images is a first image whose feature amount related to a region having a bubble or a residue imaged is equal to or greater than a predetermined amount;

determining, by the processor, whether the images that have been determined to be the first image continue a predetermined number of times; setting, by the processor, the imaging frame rate based on a predetermined number of continuous images that have been determined to be the first image, and changing, by the processor, the imaging frame rate in the image sensor to the set imaging frame rate.

* * * * *